United States Patent [19]

Gonser

[11] Patent Number: 4,505,676
[45] Date of Patent: Mar. 19, 1985

[54] ENDODONTIC UNIT
[75] Inventor: Donald I. Gonser, York, Pa.
[73] Assignee: Dentsply Research & Development Corp., Milford, Del.
[21] Appl. No.: 537,906
[22] Filed: Sep. 30, 1983
[51] Int. Cl.$^3$ ............................................. A61C 1/07
[52] U.S. Cl. .................................... 433/119; 433/86; 433/127
[58] Field of Search ............... 433/118, 119, 122, 123, 433/124, 127, 128, 129, 86; 279/86, 97, 99

[56] References Cited
U.S. PATENT DOCUMENTS

| | | | |
|---|---|---|---|
| 2,545,521 | 3/1951 | Knapik | 433/147 |
| 3,375,583 | 4/1968 | Blank et al. | 433/86 |
| 3,956,826 | 5/1976 | Perdreaux, Jr. | 433/86 |
| 4,295,827 | 10/1981 | Martin et al. | 433/119 |
| 4,330,278 | 5/1982 | Martin | 433/86 |

Primary Examiner—John J. Wilson
Attorney, Agent, or Firm—Edward J. Hanson, Jr.; C. Hercus Just

[57] ABSTRACT

An endodontic unit comprising an elongated ultrasonic oscillating body having a tubular conduit extending beyond one end and provided with a weighted head on the outer end and in which a socket is formed and disposed at an obtuse angle to the axis of the body by means of providing a bend in the conduit intermediately of the ends thereof subtending an obtuse angle of greater magnitude than the obtuse angle of the socket, the weight of the head being adequate to damp the vibrations imposed upon an endodontic file, when mounted in the socket, to a degree sufficient to minimize the breakage of files and also induce in the files desired vibratory and oscillating movement to effect efficient operation in endodontic performance.

3 Claims, 4 Drawing Figures

U.S. Patent  Mar. 19, 1985  4,505,676
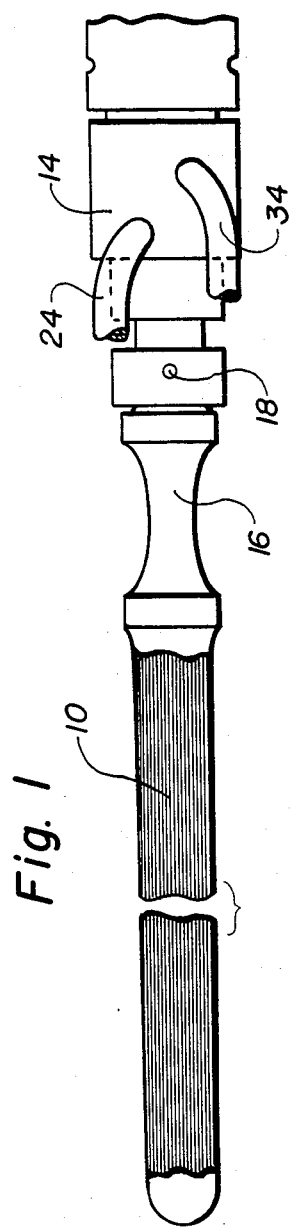
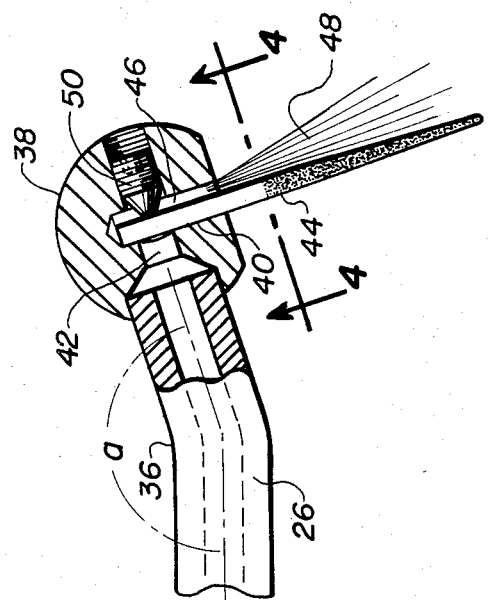
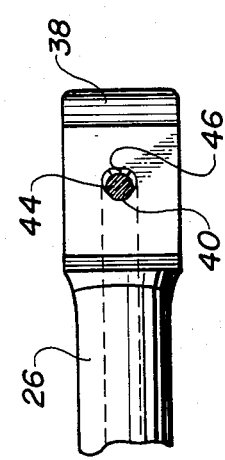
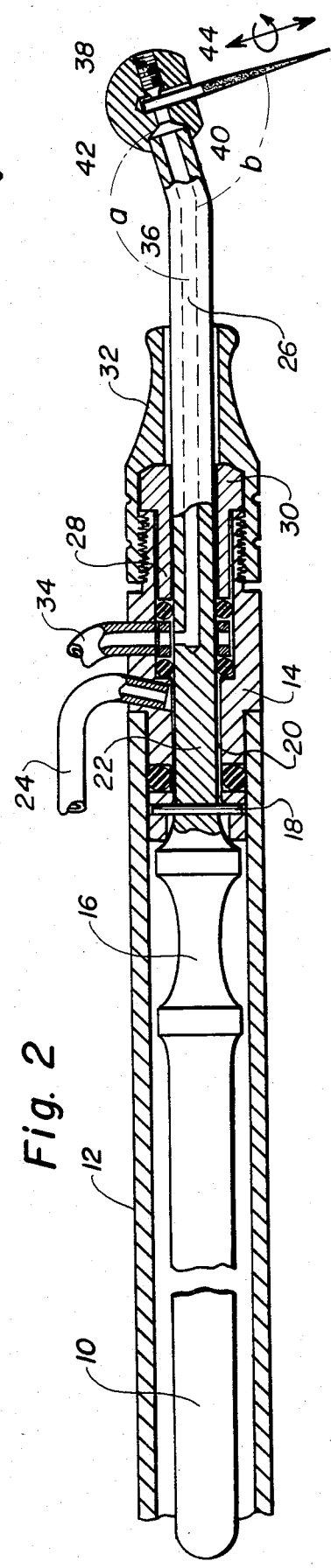

ENDODONTIC UNIT

BACKGROUND OF THE INVENTION

The use of rather delicate instruments known as endodontic files for the manual extraction of nerves from the root canals of teeth is well-known. Such an operation is relatively slow and it is difficult to completely clean the canal of the material desired to be removed therefrom, such as nerve fragments, followed for example, by irrigation of the canal to flush the same, as a separate operation from the use of the file. Accordingly, previous attempts have been made to provide mechanically-operated files and several of these respectively comprise the subject matter of prior U.S. Pat. Nos. 4,295,827, issued Oct. 20, 1981, and 4,330,278, issued May 18, 1982, both in the name of Howard Martin. Both of these patents, in addition to providing means to hold a dental file, also provide means to irrigate the canal.

In additon to operating endodontic files and irrigating the cavities or root canals, it has been found that the use of a solution of 2.5% sodium hypochlorite or the like, has the added advantage of also facilitating dissolving collagen within the canal, as well as killing any microorganisms which may be present in the canal. Said solution, however, is very corrosive to certain metals and particularly Monel metal and certain previous attempts to utilize an ultrasonic handpiece to hold and drive the endodontic file have attempted to employ Monel tubes to deliver the hypochlorite solution to the root canals. Because of the relatively high reaction of the solution of the Monel metal, however, the tubular supports were found to have relatively short life. Incident to using the hypochlorite solution, it also is necessary to use a rubber dam of conventional type in the oral cavity and merely expose the tooth upon which operation is being performed, a high volume evacuator or the like also being employed to remove the solution as rapidly as possible for safety to the patient.

It also has been found that one type of power means which can be employed to vibrate or oscillate an endodontic file is an ultrasonic handpiece primarily designed to perform prophylactic operations by dental hygienists and the like, several examples of which are shown in the following prior U.S. Pat. Nos.:

3,375,583, dated Apr. 2, 1968 to Blank et al
3,956,826, dated May 18, 1976 to Perdreaux, Jr.

The use of such devices as those now commonly employed to support relatively delicate endodontic files has been found to result in frequent and substantial breakage of the files due to the amount of power supplied. Accordingly, while it is believed that this type of power is adapted to be used for endodontic operations, the aforementioned problem requires a solution and the present invention is believed to be a useful solution to the problem of insuring substantial endodontic file life.

Another problem existing in the attempted solution to providing a suitable power device comprises attempts to employ stainless steel, which is not affected to any appreciable extent by the use of sodium hypochlorite, rather than Monel metal, but in substituting stainless steel, it has been found that the very high frequency of ultrasonic dental handpieces, such as used by hygienists, generates very substantial heat to the stainless steel elements which support the files, whereby it is essential to deliver a suitable coolant to the stainless steel members.

In general, therefore, the present invention has contemplated all of the foregoing problems and now provides what is believed to be practical solutions to solving the same, details of the improvements being set forth below.

SUMMARY OF THE INVENTION

Among the principal objectives of the present invention is the provision of adapting to an ultrasonic oscillating body member for purposes of driving an endodontic file, a tubular conduit stem connected at one end to the operating end of the body member for vibration of the tube at ultrasonic values and mounting a weighted head of predetermined degree or amount upon the outer end of said tube, the tube being of stainless steel and having a bend therein between the opposite ends thereof which subtend an obtuse angle therebetween, and said head having a socket opening outwardly therefrom along an axis substantially perpendicular to the end portion of the tube which is immediately secured to the head, thereby disposing the axis of a file when mounted in said socket at an obtuse angle with respect to the axis of the oscillating body of a lesser degree than the aforementioned obtuse angle, whereby when an endodontic file is mounted in said socket, the angular relationship thereof with respect to the ultrasonic oscillating body results in producing in the file not only axially-extending vibratory motion, but also lateral oscillatory or somewhat rotary motion, all of which motions facilitate the performance of the file with respect to cleansing of a root canal, for example, together with applying flushing medicament thereto to remove the debris from the root canal, and incidentally render the same hygienic with respect to any existing microorganisms.

Another object of the invention is to select and calibrate the weight of the aforementioned head on the outer end of the tubular conduit stem so as to suitably dampen the driving effect imposed upon the same by the ultrasonic oscillating body and to a large extent remove the resonance of the ultrasonic oscillating body upon the endodontic file while simultaneously reciprocating and/or oscillating the dental file in the manner referred above and distributing the forces imposed upon the file in such manner as to prevent breakage thereof.

A further object of the invention is to arrange the obtuse angle in said conduit stem so as to be approximately 165° and the obtuse angle of the axis of said socket is approximately 105°.

Details of the foregoing objects and of the invention, as well as other objects thereof, are set forth in the following specification and illustrated in the accompanying drawing comprising a part thereof.

BRIEF DESCRIPTION OF THE DRAWING

FIG. 1 is a side elevation of the power-supplying element of an ultrasonic dental handpiece attached to fragmentarily illustrated portion of the fluid-distributing members for the handpiece.

FIG. 2 is a longitudinal sectional view of the portion of the handpiece shown in FIG. 1, and additionally showing in greater detail the medicament and cooling liquid distributing means delivered to a tubular conduit stem having a weighted head on the outer end thereof, showing the bend disposed in said tube intermediately of the ends thereof as indicated by obtuse angle indications.

FIG. 3 is a further enlarged partially sectional view of a fragmentary outer end portion of the tube and head shown in FIG. 2, and illustrating particularly the discharge means for medicament to direct the same longitudinally along a file mounted in said head.

FIG. 4 is a fragmentary view of the lower surface of the portion of the unit shown in FIG. 3, as seen on the line 4—4 thereof.

DETAILED DESCRIPTION OF THE PREFERRED EMBODIMENTS

Referring to FIG. 1, there is illustrated at the left-hand end thereof the power element of an ultrasonic dental handpiece comprising a stack of magnetostrictive laminations 10 comprising a stack which, when excited by suitable high frequency alternating current, produces ultrasonic vibrations of a high degree such as of the order of 25,000 vibrations per second. It will be understood that said stack is mounted within a suitable handle containing driver and feedback coils 12, fragmentarily shown in FIG. 2, and connected to one end of the stack 10 is a body member 14 made of suitable stainless steel which has a longitudinal bore therein receiving one end of a connector 16 which is affixed by a transverse pin 18 to the body member 14 to impart driving movement to the body by means of operation of the magnetostrictive stack 10.

It also will be seen that there is a space 20 between the bore of body member 14 and the transformer portion 22 of the member 16 which extends through said bore to permit the passage of fluid therebetween as cooling fluid, as the stack generates heat, and is directed into the space from conduit 24. Such coolant may be cool water or the like. The forward portion of the portion 22 of connector 16 is provided with a longitudinal central bore and comprises a tubular conduit stem 26. A cylindrical plug 28 has a collar 30, which abuts the outer end of body member 14, as clearly shown in FIG. 2, and is held against said end of the body by means of a threaded sleeve 32. Both the plug 28 and sleeve 32 have inner diameters greater than that of conduit stem 26, thereby providing a fluid passage for the coolant referred to above, which may be discharged along the outer end of the conduit stem 26, which projects beyond the outer end of threaded sleeve 32.

The inner end of the conduit stem 26 communicates with another conduit 34 through which suitable medicaments, such as a desirable solution of sodium hypochlorite is obtained from a suitable supply, not shown, for delivery to the outer end of the conduit stem 26. It also will be understood that the conduit 24 is connected to a suitable source of coolant, water, or otherwise, not shown.

Referring to FIGS. 2 and 3, it will be seen that the conduit stem 26 is provided intermediately of the opposite end thereof with a bend 36, whereby the portions of the stem which are on opposite sides of said bend respectively subtend an obtuse angle a of approximately 165°, which is for purposes to be described. Affixed to the outer end of stem 26 is a weighted head 38 provided with a socket 40 with which a transverse opening 42 communicates somewhat as an extension of the longitudinal opening of the conduit stem 26. As a result, this arrangement disposes the axis of the socket 40 at an obtuse angle b of lesser amount than obtuse angle a and comprising an obtuse angle of approximately 105°. It is to be understood that the specific designations of these obtuse angles are to be considered substantially optimum rather than absolutely restrictive since a few degrees of difference will still provide an operative device. The socket 40 receives the shank end of an endodontic file 44, the shank of which is at least slightly less than that of the diameter of the bore 40 in order to provide a space 46 through which fluid, such as medicament, may be discharged and will be directed longitudinally along the file 44, somewhat in the form of a spray 48, which will be directed into the root canal or other cavity formed in a natural tooth in accordance with endodontic techniques.

Due to the fact that the socket 40 is of greater diameter than the shank of the file 44, for purposes of providing the discharge space 46, it is necessary to secure the shank of the file within the socket in such manner that fluid can pass around the same to form the discharge spray 48, and this is accomplished by securing the shank end of the file within the socket 40 by a suitable set screw, such as an Allen set screw 50, which may be operated by a suitable Allen wrench in conventional manner, and has been found to be highly effective for purposes of securing an endodontic file within the weighted head 38. The space 46 also is shown in FIG. 4 in such manner as to illustrate communication between said space and the bore within the tubular conduit stem 26. It also is to be understood that the specific illustration of the outer end of the file 44 is purely exemplary of any of a number of desirable cutting or scraping configurations employed in endodontic files.

Utilization of the bend 36 primarily is for two purposes, the first and more important of which is to especially dispose the axis of the file 44 at the desired obtuse angle b with respect to the axis of the conduit stem 26, and this arrangement has been found to be of importance in minimizing the breakage of files due to the forces imposed upon the same by the ultrasonic oscillating body member composed of the stack 10 and connector 16, but in conjunction with the weighted head 38. In this regard, the weight of the head can best be determined empirically, but the mass thereof must be such that it is adequate to dampen the energy supplied by the ultrasonic magnetostrictive stack 10 and this, in cooperation with the directing of the vibrations and oscillations of the file 44 by means of the bend 36, has been found to result in vast minimizing of the breakage of endodontic files, especially by changing the configuration of the movement of the operating end of the file in which there is both vertical (axial) or compression movement, as well as lateral flexural movement which may be either oscillatory or somewhat rotary, all of which very efficiently operates upon matter to be removed from a root canal or the like, such as root material. Further, in conjunction with the provision of the flushing means described above, such flushing automatically and simultaneously occurs while the above-described movements of the file occur to produce an overall, combined efficient endodontic treatment of a root canal or similar cavity in a human tooth.

In addition to the foregoing, the use of stainless steel in forming the tubular conduit stem, 26, as well as the connector 16 and portion 22 thereof, prevents corrosion by the preferred medicament described above, sodium hypochlorite, which is useful to dissolve collagen within an oral cavity, as well as killing any microorganisms which similarly may exist in such canal. Constant flushing of the conduit stem 26 by a coolant conduit 24, for example, maintains the same cool so as to prevent injury to any portion of an oral cavity in which the endodontic unit is being employed, and such coolant also facilitates flushing the unit to remove the medicament therefrom, at least to a desirable degree.

From the above discussion, it will be understood that the ultrasonically axially oscillating member 10 has an extension means 36 thereon which has a limited modulus of elasticity, preferably being made of stainless steel. The extension means 36 is connected to the ultrasonically axially oscillating member and extends at an obtuse angle therefrom. A weighted head 38 is mounted on the extension means 36 remote from the ultrasonically axially oscillating member 10. The weighted head is weighted and positioned to dampen the ultrasonic axial oscillating member's axial oscillation and magnify obtuse oscillation from the extension means through the limited modulus of elasticity of the stainless steel extension member. The extension means extends obtusely from said axial member reverse to the direction of projection that a file will take when secured in the handpiece and the head is mounted on the extension means at the extension's outer extremity. When the ultrasonic endodontic handpiece is activated, axial forces are created and some of the axial forces are converted by the angle of the extension means to vector forces whereby a file mounted in the handpiece has significant up and down abrading motion as well as back and forth motion in the line of the axial oscillation of said ultrasonically axially oscillating member.

The foregoing description illustrates preferred embodiments of the invention. However, concepts employed may, based upon such description, be employed in other embodiments without departing from the scope of the invention. Accordingly, the following claims are intended to protect the invention broadly, as well as in the specific forms shown herein.

It is claimed:

1. An endodontic unit to support and vibrate an endodontic file comprising in combination, an ultrasonic oscillating body member adapted to be energized to oscillate in ultrasonic ranges and having an operating end, a tubular conduit stem connected at one end with said operating end of said body member for vibration thereby and having a portion projecting longitudinally beyond said operating end of said member, a weighted head of predetermined amount connected to the outer end of said stem and having a socket opening outwardly from said head and communicating with said stem, means connected respectively to said stem and to a source of liquid medicament to supply the same to said socket for discharge therefrom, said stem having a first obtuse angle therein of approximately 165° intermediate of the ends of the portion thereof extending beyond said body member, thereby to dispose the axis of said socket at a second obtuse angle of approximately 105° to the longitudinal axis of said body member, said socket having a larger diameter than the shank of a file adapted to be mounted in said socket, whereby a space is provided in said socket which communicates with the opening in said stem to receive liquid medicament therefrom and discharge it longitudinally along a file when the same is affixed within said socket, and means on said head to secure a file within said socket.

2. The endodontic unit according to claim 1 in which at least said tubular conduit stem is formed of stainless steel to resist corrosion by said medicament and said means in said head to secure a file within said socket comprises a set screw operable to clamp the shank of the file firmly against one sidewall of said socket in a manner to provide ready passage of liquid medicament from said socket and along said file as aforesaid.

3. The endodontic unit according to claim 1 in which the amount of weight of said weighted head being selected to act as dampening means for the ultrasonic output of said oscillating body which in conjunction with the angle of the axis of said socket relative to the axis of the oscillating body produces a desired value of vibrating movement of the file in both axial and lateral directions adequate to minimize breakage of endodontic files when operated by said oscillating body.

* * * * *